(12) United States Patent
Sorger et al.

(10) Patent No.: US 6,603,034 B2
(45) Date of Patent: Aug. 5, 2003

(54) PREPARATION OF ORGANOZINC HALIDES FROM REACTIVE HALOGEN COMPOUNDS AND THEIR USE

(75) Inventors: Klas Sorger, München (DE); Hermann Petersen, Burghausen (DE); Jürgen Stohrer, Pullach (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 0 days.

(21) Appl. No.: 10/308,397

(22) Filed: Dec. 3, 2002

(65) Prior Publication Data

US 2003/0114697 A1 Jun. 19, 2003

(30) Foreign Application Priority Data

Dec. 13, 2001 (DE) .......................... 101 61 335

(51) Int. Cl.$^7$ ............. C07F 3/06; C07C 67/00; C09K 3/00
(52) U.S. Cl. ............. 556/128; 560/208; 560/209; 560/210; 560/215; 252/182.11
(58) Field of Search ............. 556/128; 252/182.11; 560/208, 209, 210, 215

(56) References Cited

U.S. PATENT DOCUMENTS 5,294,731 A    3/1994 Paust et al. .................. 560/60
5,964,919 A  * 10/1999 Rieke .......................... 75/362
2002/0013501 A1  1/2002 Sorger et al. ................ 564/463

FOREIGN PATENT DOCUMENTS

| EP | 562343 | 9/1993 | |
| EP | 562343 A1 * | 9/1993 | ......... C07C/67/343 |
| EP | 1167325 | 1/2002 | |
| SU | 472127 | 2/1976 | |

OTHER PUBLICATIONS

Database WPI, Section Ch, Week 197634, Derwent Publications, AN 1976–64551x, XP002230110.
Forstner, A., "Recent Advancements in the Reformatsky Reaction ", Synthesis, 1989, pp. 571–590.
English Derwent Abstract AN 1993–304777 corresponding to EP562343.
English literal translation of SU472127.
A. Forstner, Synthesis 1989, pp.571–590.

* cited by examiner

Primary Examiner—Porfirio Nazario-Gonzalez
(74) Attorney, Agent, or Firm—Collard & Roe, P.C.

(57) ABSTRACT

A process for preparing organozinc halides in solvents, includes reacting a reactive halogen compound with zinc in one or more carboxylic esters. It is also possible to prepare keto, hydroxyl and amino compounds of organozinc halides obtained in a first step from a reactive halogen compound and zinc in one or more carboxylic esters, wherein the organozinc halide obtained is reacted in a second step with an electrophilic reaction partner and the reaction product of the second step is hydrolyzed in a third step.

10 Claims, No Drawings

PREPARATION OF ORGANOZINC HALIDES FROM REACTIVE HALOGEN COMPOUNDS AND THEIR USE

BACKGROUND OF THE INVENTION

1. Field of the Invention

The present invention relates to a process for preparing organozinc halides (halogen-zinc compounds, Reformatsky reagents) from reactive halogen compounds and to their use in preparing keto, hydroxyl and amino compounds in carboxylic esters.

2. The Prior Art

The reaction of reactive halogen compounds, in particular of α-halocarbonyl compounds, with electrophilic substrates, for example aldehydes, ketones, imines, nitriles, carboxylic anhydrides, carboxylic chlorides, lactones, orthoformates, formates, epoxides, azirines, aminals and nitrones, in the presence of zinc metal, is known as the Reformatsky reaction. This reaction produces important synthetic building blocks for preparing active pharmaceutical ingredients, scents and crop protecting agents.

The choice of the solvent and the activation of the zinc used or of the entire reaction mixture are of decisive importance for the achievement of good yields and high selectivities and therefore good product purities.

It is known that particularly useful solvents for the Reformatsky reaction include ethers such as diethyl ether, 1,4-dioxane, dimethoxymethane, dimethoxyethane and in particular tetrahydrofuran. In addition, further solvents which have proven useful include aromatic hydrocarbons or mixtures of the abovementioned ethers with aromatic hydrocarbons, the mixture of tetrahydrofuran with trimethyl borate, and the polar solvents acetonitrile, dimethylformamide, dimethyl-acetamide, dimethyl sulfoxide and hexamethyl-phosphoramide. A review on this subject is contained, for example, in A. Fürstner, *Synthesis* 1989, pp. 571–590.

EP-A-562 343 discloses that the reaction of α-bromocarboxylic esters with carbonyl compounds in the presence of zinc in the solvent methylene chloride proceeds with high yields.

The use of the solvents and solvent mixtures mentioned has the following disadvantages:

the water-miscible ethers 1,4-dioxane and tetrahydrofuran and also the water-miscible polar solvents acetonitrile, dimethylformamide, dimethylacetamide, dimethyl sulfoxide and hexamethylphosphoramide dissolve in the aqueous phase on aqueous workup to hydrolyze the zinc compounds and zinc salts formed.

Particularly when applied on the industrial scale, it is necessary, for economic reasons and to reduce the amounts of waste, and to recover the solvents used from the aqueous phase. This recovery may be done for example by extraction or distillation, which is, however, associated with considerable cost and inconvenience.

In addition, when the abovementioned water-miscible solvents are used in the hydrolysis of the reaction mixture, it is customarily necessary to use water-immiscible organic solvents such as ethyl acetate or methyl tert-butyl ether as cosolvents for better phase separation. These solvents have to be recovered and, before reuse, freed of impurities by distillation, which is likewise associated with high cost and inconvenience. When solvent mixtures are used for Reformatsky reactions, the recovery, separation and any purification of the individual solvents used generally entails even more considerable cost and inconvenience.

Furthermore, when diethyl ether, 1,4-dioxane, dimethoxymethane, dimethoxyethane and tetrahydrofuran are used as solvents for Reformatsky reactions, they tend to form explosive peroxides by autoxidation. This makes their use on the industrial scale dangerous, in particular on repeated use after recovery (danger of accumulation of the explosive components). Or it makes their use more difficult or possible only at great cost and inconvenience.

The use of methylene chloride as solvent, as disclosed by EP-A-562 343, or of other halogenated hydrocarbons as solvents is objectionable for environmental reasons. Accordingly it is to be avoided, on the industrial scale in particular. In addition, many of the abovementioned solvents are expensive which additionally compromises the economic viability of the reaction without recovery of the solvent used.

SU 472127 discloses the reaction of α-bromoketones and zinc with nitriles in ethyl acetate as solvent for preparing α-iminoketones. A mixture of bromoketone (reactive halogen compound) and nitrile (electrophilic substrate) is added to activated zinc, and the organozinc halide formed (Reformatsky reagent) reacts immediately with the substrate. For many substrates, the addition of a mixture of reactive halogen compound and electrophilic substrate described in SU 472127 is highly disadvantageous.

Certain substrates which have further functional groups, for example amino or epoxide functionalities, react as soon as they are combined with the reactive halogen compound (for example α-haloester, α-bromoketone). They form undesired by-products before the actual contact with the zinc takes place. For instance, those skilled in the art are familiar with the reaction of amines or epoxides with reactive halogen compounds, for example from X.-P. Gu, I. Ikeda, M. Okahara, *Bull. Chem. Soc. Jpn.*, 1987, 60, pp. 397–398. The process described is accordingly unsuitable for such substrates.

SUMMARY OF THE INVENTION

It is an object of the present invention to provide a process which solves the problems known from the prior art.

The present invention provides a process for preparing organozinc halides in solvents, which comprises reacting a reactive halogen compound with zinc in one or more carboxylic esters.

In a preferred embodiment of the invention, the process according to the invention is used to prepare organozinc halides of the general formula (4)

$$\text{HalZn}-R^3R^4C-(X)_1-Y \qquad (4)$$

by reacting reactive halogen compounds of the general formula (2)

$$\text{Hal-}R^3R^4C-(X)_1-Y \qquad (2)$$

with zinc, where $R^1$ and $R^2$ are each hydrogen or an optionally halogen- or cyano-substituted $C_1$–$C_{30}$-hydrocarbon radical in which one or more nonadjacent methylene units may be replaced by —O—, —CO—, —COO—, —OCO—, or —OCOO—, —S— or —$NR^x$— groups and in which one or more methine units may be replaced by —N= or —P= groups, $R^3$, $R^4$, $R^5$, $R^6$ and $R^7$ are each hydrogen, halogen or an optionally halogen-substituted or cyano-substituted $C_1$–$C_{30}$-hydrocarbon radical in which one or more nonadjacent methylene units may be replaced by —O—, —CO—, —COO—, —OCO—, or —OCOO—, —S— or —NR$^x$— groups and in which one or more methine units may be replaced by —N═ or —P═ groups, X is selected from

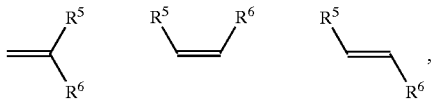

l is an integer having the value 0 or 1,
Y is CN, (C═O)—Z, (SO$_2$)—Z, (P═O) (—Z)$_2$, R$^5$C═CR$^6$R$^7$, C≡C—R$^5$
or an aromatic radical in which one or more methine units in the ring may be replaced by —N═ or —P═ groups and which may carry the heteroatoms —O—, —S— or —NH— in the ring, where the aromatic ring is optionally halogen- or cyano-substituted or is substituted by C$_1$–C$_{30}$-hydrocarbon radicals in which one or more nonadjacent methylene units may be replaced by —O—, —CO—, —COO—, —OCO—, or —OCOO—, —S— or —NR$^x$— groups, Z is an optionally halogen-substituted C$_1$–C$_{30}$-hydrocarbon radical in which one or more nonadjacent methylene units may be replaced by —O—, —CO—, —COO—, —OCO—, —OCOO—, —S— or —NR$^x$— groups and in which one or more methine units may be replaced by —N═ or —P═ groups, OH, OR$^1$, OSi (R$^3$)$_3$, NHR$^1$ or NR$^1$R$^2$, Hal is chlorine, bromine or iodine,
R$^x$ is hydrogen or an optionally halogen-substituted C$_1$–C$_{30}$-hydrocarbon radical in which one or more nonadjacent methylene units may be replaced by —O—, —CO—, —COO—, —OCO—, or —OCOO—, —S—, —NH— or —N—C$_1$–C$_{20}$-alkyl groups and in which one or more methine units may be replaced by —N═ or —P═ groups, and pairs of radicals selected from R$^1$ and R$^2$, R$^3$ and R$^4$, R$^4$ and R$^5$, R$^5$ and R$^6$, R$^6$ and R$^7$, R$^1$ and R$^3$, R$^1$ and Y, R$^1$ and Z, R$^3$ and Y, R$^3$ and Z, R$^5$ and Y, R$^5$ and Z, where Z may be a direct bond, may each be linked to each other.

The invention further provides the use for preparing keto, hydroxyl and amino compounds of organozinc halides obtained in a first step from a reactive halogen compound and zinc in one or more carboxylic esters, wherein the organozinc halide obtained is reacted in a second step with an electrophilic reaction partner and the reaction product of the second step is hydrolyzed in a third step.

Preference is given to using the process according to the invention for preparing keto, hydroxyl and amino compounds of the general formula (1)

R$^1$(R$^2$)$_k$C(W$^x$)—R$^3$R$^4$C—(X)$_l$—Y    (1)

wherein the electrophilic reaction partner used in the second step is an aldehyde, ketone or imine of the general formula (5a)

R$^1$R$^2$C═W    (5a)

or an epoxide of the general formula (5b)

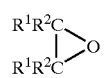    (5b)

or a nitrile of the general formula (5c)

R$^1$C≡N    (5c)

or a carboxylic halide of the general formula (5d)

R$^1$(C═O)-Hal    (5d)

where
W$^x$ is OH, NHR$^1$ or ═O and
W is O or NR$^1$,
k when W$^x$ is OH and NHR$^1$, should have the value 1 and, when W$^x$ is ═O, should have the value 0, and
the remaining radicals are defined above and in addition pairs of 2 radicals selected from R$^1$ and R$^2$, R$^3$ and R$^4$, R$^4$ and R$^5$, R$^5$ and R$^6$, R$^6$ and R$^7$, R$^1$ and R$^3$, R$^1$ and Y, R$^1$ and Z, R$^3$ and Y, R$^3$ and Z, R$^5$ and Y, R$^5$ and Z, W$^x$ and Y and also W$^x$ and Z, where W$^x$ is O— or NR$^1$— and Z may be a direct bond, may each be linked to each other.

The invention further provides solutions of organozinc halides in carboxylic esters which are prepared by the process according to the invention.

It has surprisingly been found that carboxylic esters are on the one hand suitable solvents for preparing organozinc halides (Reformatsky reagents) from reactive halogen compounds and zinc.

Furthermore, carboxylic esters are also outstandingly suitable for further reactions of the halogen-zinc compounds with electrophilic substrates (Reformatsky reaction), in particular with aldehydes, ketones, imines, nitrites, carboxylic halides and epoxides, and also for the subsequent hydrolysis of the reaction products obtained in this way in a further reaction step.

In this way, keto, hydroxyl and amino compounds in particular can be prepared.

The use of carboxylic esters as solvents makes it possible to carry out the reaction on the industrial scale in particular without the addition of further solvents or cosolvents or the use of solvent mixtures. The reaction occurs with high yields and selectivities while at the same time allowing simple recovery of the solvent used. As a consequence the reaction occurs in an environmentally friendly and cost-effective manner, since the amounts of waste can be markedly reduced.

The Reformatsky reagents prepared by the process according to the invention in the form of organozinc halides dissolved in carboxylic esters are surprisingly stable as reactive organometallic intermediates over long periods even at relatively high temperatures. They may be reacted further immediately or not until a later time in subsequent reaction steps, in particular with electrophilic substrates.

The Reformatsky reagents prepared by the process according to the invention in the form of organozinc halides dissolved in carboxylic esters therefore constitute reaction-ready solutions. They are universally usable starting compounds for reactions with electrophiles, in particular for Reformatsky reactions.

The above-described process according to the invention allows keto, hydroxyl and amino compounds of the general formula (1) to be obtained in very high yields of up to >90% and very high purities in a simple manner and at simultaneously very good space-time yields.

The process according to the invention is simple to perform, particularly on the industrial scale. This is because the reaction may be carried out in the commercially obtainable carboxylic esters of the general formula (3) as solvents without pretreatment of these solvents, for example distillation or drying, being necessary.

The subsequent reaction steps in the form of further reactions with electrophiles, in particular of Reformatsky reactions, do not require the addition of a further solvent. For example, it is not necessary to add a cosolvent for better phase separation in the workup, either for carrying out the reaction or for the workup. Since no solvent mixtures have to be added, the solvents used can be recovered very simply. The carboxylic esters of the general formula (3) which are preferably used are only slightly or very sparingly soluble in water. Therefore they can be easily and efficiently recovered, for example in the product isolation, which makes the reaction very economical. For example, when ethyl acetate, isopropyl acetate or butyl acetate are used as the solvent of the general formula (3), they can be recovered in very high yields when the products prepared are isolated by distillation.

The processes according to the invention additionally facilitate the replacement of halogenated hydrocarbons and ethers prone to peroxide formation by carboxylic esters of the general formula (3) as the solvent. This not only makes the processes according to the invention more environmentally friendly but also markedly reduces the danger potential.

Furthermore, in many cases, the product yield and quality of the keto, hydroxyl and amino compounds of the general formula (1) prepared according to the process variant according to the invention are improved compared to the existing variants described in the literature. The use of carboxylic esters of the general formula (3) is particularly advantageous for the progress of the reaction, the product yields and purities and the elimination of secondary reactions.

In addition, the processes according to the invention may be performed in most cases with a slight excess of zinc and reactive halogen compound of the general formula (2), based on the electrophilic reaction partner. This results in many cases in higher product yields and qualities than in existing variants using the previously known solvents mentioned. This makes the process according to the invention particularly economical.

Furthermore, the process according to the invention advantageously also makes it possible to react electrophilic substrates which have nucleophilic functional groups (for example amino groups) or nucleophilic properties (for example epoxides). They react as soon as they are combined with the reactive halogen compound forming undesired by-products even before contact with the zinc. However, the organozinc halide prepared in the first reaction step of the process according to the invention from reactive halogen compound and zinc is reacted in the second reaction step with the substrates (for example epoxides or substrates having amino groups) in high yields and high purities to be changed into the desired products without forming undesired by-products (See Example 5).

In addition, it is possible for the organozinc halides prepared in the first step of the process according to the invention to be reacted with the electrophiles in a second step under mild conditions at low temperature to obtain high yields and in particular high purities. This allows electrophilic reaction partners, for example epoxides, which are particularly sensitive and unstable at relatively high temperatures as are required for preparing the organozinc halides in the first step to be reacted with high yields and product purities. In contrast, when a mixture of bromoacetic ester and styrene oxide is reacted with zinc at an elevated temperature of 55–65° C., as described in SU 472127, the drastic reaction conditions result in decomposition of the reaction mixture to form undesired by-products (See Comparative Example 7).

Also, the organozinc halides prepared in the first reaction step can initially be stored stably or intermediately stored before reaction with the electrophilic reaction partner. This is advantageous in particular in industrial implementation, since this allows industrial production processes to be configured optimally in terms of time, personnel and capacity, and to be run in parallel. This which makes the process according to the invention particularly economical in particular when carried out on the industrial scale.

The $C_1$–$C_{30}$-hydrocarbon radicals for $R^1$, $R^2$, $R^3$, $R^4$, RS and Z are preferably linear, branched or cyclic $C_1$–$C_{20}$-alkyl, $C_3$–$C_{20}$-alkoxycarbonylalkyl, $C_2$–$C_{20}$-alkenyl, $C_5$–$C_{20}$-acetalalkenyl or $C_3$–$C_{20}$-alkoxycarbonylalkyl radicals, each of which may be substituted by F, Cl, Br, I, CN or $C_1$–$C_8$-alkoxy radicals; aryl, aralkyl, alkaryl, aralkenyl or alkenylaryl radicals in which one or more methine units may be replaced by —N= or —P= groups and methylene units by —O—, —S— or —NH—, each of which may be substituted by F, Cl, Br, I, CN, $C_1$–$C_{10}$-alkoxy radicals or $C_1$–$C_{20}$-alkylamino radicals and, on the ring, by $C_1$–$C_{10}$-alkyl radicals and may carry the heteroatoms —O—, —S— or —NH— in the ring.

The radicals $R^1$ and $R^2$, $R^3$ and $R^4$, $R^4$ and $R^5$, $R^5$ and $R^6$, $R^6$ and $R^7$, $R^1$ and $R^3$, $R^3$ and Y, $R^3$ and Z, $R^3$ and Y, $R^3$ and Z, $R^5$ and Y, $R^5$ and Z, $W^x$ and Y, and $W^x$ and Z, where $W^x$ is O— or $NR^1$— and Z may be a direct bond, may be linked to each other. The radicals $R^1$ and $R^3$, $R^1$ and Y, $R^1$ and Z, $W^x$ and Y, and $W^x$ and Z, where $W^x$ is O— or $NR^1$— and Z may be a direct bond, may be linked to each other by intramolecular reaction.

The halogen radicals $R^3$, $R^4$, $R^5$, $R^6$ and $R^7$ are preferably F and Cl.

In particular, 1 has the value 0.

The reactive halogen compounds of the general formula (2) used are preferably bromine compounds, where Hal in the general formula (2) is bromine. Preference is given to reactive halogen compounds of the general formula (2) in which Y is (C=O)—Z. Preference is further given to reactive halogen compounds of the general formula (2) in which Z is $OR^1$. In particular, preference is given to α-bromocarboxylic esters as the reactive halogen compounds of the general formula (2).

In the use according to the invention of organozinc halides in a process for preparing keto, hydroxyl and amino compounds, preference is given to initially charging the zinc in the carboxylic ester of the general formula (3) in a first step and then adding the reactive halogen compounds of the general formula (2), optionally dissolved in a solvent.

In a second step, suitable electrophilic substrates, preferably aldehydes, ketones, imines, epoxides, nitrites and carboxylic halides of the general formulae (5a) to (5d), optionally dissolved in a solvent, are added to the solution of the organozinc halides of the general formula (4) obtained in the first step.

Preference is likewise given to adding the solution of the organozinc halides of the general formula (4) obtained in the first step to suitable electrophilic substrates. These substrates are preferably aldehydes, ketones, imines, epoxides, nitriles and carboxylic halides of the general formulae (5a) to (5d), optionally dissolved in a solvent, in a second step.

A. Fürstner, *Synthesis* 1989, pp. 571–590 and K. Nützel in Houben-Weyl, *Methoden der organischen Chemie*, 4th edition, Vol. XIII/2a, Stuttgart 1973, pp. 828–832 disclose that α-bromozinc esters (Reformatsky reagents) of the general formula (4) can react with certain reactive carboxylic esters, viz. cyclic carboxylic esters (lactones), formic esters, orthoformic esters and benzoic esters. Reactive carboxylic esters other than those mentioned above are not reactive toward α-bromozinc esters. In exceptional cases, a reaction does take place either when coordinating or polar solvents (for example 1,4-dioxane or dimethyl sulfoxide) are used or when the reaction times are long and temperatures are high at the same time.

Surprisingly, the organozinc halides (Reformatsky reagents) of the general formula (4) prepared by the process according to the invention are sufficiently stable and storable (see examples) in the carboxylic esters of the general formula (3). These esters can be used as solvent in the process according to the invention even at elevated temperatures. They can be converted directly to keto, hydroxyl or amino compounds in subsequent reaction steps by reaction with electrophilic substrates and hydrolysis, which would not have been expected on the basis of the teachings of the prior art.

During the preparation of the organozinc halides by the process according to the invention, the temperature of the exothermic reaction is generally maintained at a predetermined value, if necessary by cooling. The upper temperature limit may be defined by the boiling point of the solvent of the general formula (3) used, for example ethyl acetate (b.p.: 77° C.) or isopropyl acetate (b.p.: 87–89° C.). In the case of higher-boiling solvents of the general formula (3), for example n-butyl acetate (b.p.: 124–126° C.), preference is given to controlling the temperature of the reaction by cooling. Preference is given to carrying out the reaction at temperatures of from −20 to +150° C., more preferably from 20 to 110° C., in particular from 40 to 90° C.

Zinc is generally used in the form of sheets, ribbon, turnings, powder or dust, or in the form of zinc wool. The presence of other metals such as copper, silver or mercury is not necessary. In particular, zinc is used in the form of commercially obtainable, commercially customary zinc powder or zinc dust. Preference is given to zinc of high purity of at least 99.995%, greater preference to zinc dust which is obtained from zinc having a purity of at least 99.995%.

To achieve high product yields, it has generally proven advantageous to activate the zinc before addition of the reactive halogen compound of the general formula (2). For zinc activation, existing methods which are customarily used and mentioned, for example, in the review of A F ürstner, *Synthesis* 1989, pp. 571–590, are suitable. Particularly advantageous methods have proven to be washing of the zinc with acid, activation by iodine, as described in EP-A-562 343, and the activation by trimethylchlorosilane. Particular preference is given to the activation by trimethylchlorosilane due to its ease of performance and the increased yields, product purities and selectivities, and also the suppression of secondary reactions. G. Picotin, P. Miginiac, *J. Org. Chem.* 1987, 52, p. 4796 disclose the activation of zinc by trimethylchlorosilane in the solvent diethyl ether.

To activate zinc using trimethylchlorosilane, the zinc is initially charged in the carboxylic ester of the general formula (3), then trimethylchlorosilane is added and the mixture is heated for from 10 min to 2 h, preferably from 10 to 45 min, at temperatures of from 30 to 150° C., in particular from 40 to 120° C., more preferably from 50 to 90° C. It has proven advantageous to react the zinc with trimethylchlorosilane in a molar ratio of 1:(0.005 to 0.5), in particular 1:(0.03 to 0.3) in the carboxylic ester of the general formula (3) with heating to the desired temperature.

For activation of the reaction mixture, it is also possible to add additives such as compounds of copper, chromium, manganese, cobalt, bismuth, samarium, scandium, indium, titanium, cerium, tellurium, tin, lead, antimony, germanium, aluminum, magnesium, palladium, nickel and mercury or optionally mixtures thereof.

Carboxylic esters which may be used for the processes according to the invention are preferably carboxylic esters of the general formula (3)

$$R^8-((O(CH_2)_m)_n-COO-((CH_2)_o-COO)_p-((CH_2)_q-O^9 \quad (3)$$
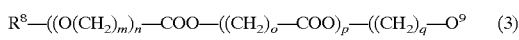

where $R^8$ and $R^9$ are each a $C_1$–$C_{30}$-hydrocarbon radical in which one or more nonadjacent methylene units may be replaced by —O— groups, and m, n, o, p, q and r are integers having values of from 0 to 6.

Preference is given in particular to those carboxylic esters of the general formula (3) in which Re and $R^9$ are preferably straight-chain, branched or cyclic $C_1$–$C_{10}$-alkyl, $C_6$–$C_{10}$-aralkyl, $C_2$–$C_{10}$-alkoxyalkyl radicals or $C_5$–$C_{10}$-aryl radicals. In particular, $R^8$ and $R^9$ are each straight-chain or branched $C_1$–$C_8$-alkyl radicals.

m, n, o, p, q and r are preferably integers having values of 0, 1, 2 or 3. In particular, n and p and r have the value 0.

Particularly preferred carboxylic esters of the general formula (3) are in particular methyl, ethyl, n-propyl, i-propyl, n-butyl, i-butyl, t-butyl, n-hexyl, n-pentyl and i-pentyl esters of acetic acid, of propionic acid and of butyric acid and ($C_6$–$C_{14}$) alkyl acetate mixtures. The esters and the ($C_6$–$C_{14}$) alkyl acetate ester mixtures may be recovered in very high yield when the products prepared are isolated and reused. When the inexpensive methyl acetate is used as the solvent of the general formula (3), recovery may be dispensed with.

After the completed reaction and the preparation according to the invention of the organozinc halides in the first step, the reaction mixture is admixed in the second step, customarily at temperatures of from −100 to +200° C., more preferably from −50 to +130° C., in particular from −30 to +80° C., with electrophilic substrates while preferably maintaining the temperature of the exothermic reaction at a predetermined value, optionally by cooling. The upper temperature limit may be defined by the boiling point of the solvent of the general formula (3) used, for example ethyl acetate (b.p.: 77° C.). Preference is given to controlling the temperature of the reaction by cooling.

Alternatively, the reaction mixture may also be added to the electrophilic substrates. After cooling of the reaction mixture at temperatures of from −20 to +30° C., the organozinc halides of the general formula (4) prepared in the first step may also initially be stored stably and reacted at a later time with electrophilic reaction partners.

After the end of the addition of all reacting components in the second step, preference is given to allowing the reaction to continue for a further from 5 min to 24 h, more preferably from 5 min to 12 h, in particular from 5 min to 8 h, in order to complete the reaction. At reaction temperatures of from 20 to 90° C., the post-reaction time is preferably from 5 min to 2 h, in particular from 5 min to 30 min.

Excess zinc metal may be removed by filtration. It is also possible to dissolve excess zinc in the acid used in the third step for hydrolysis of the reaction mixture.

It has proven useful to react the zinc with the reactive halogen compound of the general formula (2) and the electrophilic substrate of the general formulae (5a) to (5d) in a molar ratio of (1 to 3):(1 to 2):1, in particular (1.1 to 1.7):(1 to 1.3):1 in the carboxylic ester of the general formula (3) as solvent.

Furthermore, the processes according to the invention prove to be advantageous compared to existing process variants. This is because in many cases, in particular at reaction temperatures of from 20 to 80° C., the post-reaction time of from 5 to 30 min is distinctly shortened. This in particular on the industrial scale, allows very good space-time yields and accordingly very good economic viability to be achieved. Very short post-reaction times result in particular from activation of the reaction mixture or of the zinc using trialkylchlorosilane in the carboxylic ester of the general formula (3) as solvent.

After the completed reaction in the second step, the reaction mixture is hydrolyzed in the third step, customarily at temperatures of from −80 to +90° C., more preferably from −50 to +50° C., in particular from −30 to +30° C., by adding an aqueous acid or base, and zinc compounds and zinc salts which have formed are dissolved. Alternatively, the reaction mixture may also be added to an aqueous acid or base.

Preferred bases for the hydrolysis are ammonia and organic amines, such as trialkylamines and alkanolamines.

Preferred acids for the hydrolysis are Brönsted acids, in particular strong acids such as boric acid, tetrafluoroboric acid, nitric acid, nitrous acid, phosphoric acid, phosphorous acid, hypophosphorous acid, sulfuric acid, sulfurous acid, peroxosulfuric acid, hydrochloric acid, hydrofluoric acid, hydroiodic acid, hydrobromic acid, perchloric acid, hexafluorophosphoric acid, benzenesulfonic acid, p-toluenesulfonic acid, methanesulfonic acid, trifluoromethanesulfonic acid and carboxylic acids such as chloroacetic acid, trichloroacetic acid, acetic acid, acrylic acid, benzoic acid, trifluoroacetic acid, citric acid, crotonic acid, formic acid, fumaric acid, maleic acid, malonic acid, gallic acid, itaconic acid, lactic acid, tartaric acid, oxalic acid, phthalic acid and succinic acid.

In particular, ammonia, hydrochloric acid, sulfuric acid, citric acid or acetic acid, preferably ammonia, hydrochloric acid or sulfuric acid, are used. The acid or base may be used in concentrated form or in the form of a dilute aqueous solution.

The products of the general formula (1) prepared may be isolated by known, customarily used methods such as extraction, distillation, crystallization or by means of chromatographic methods. In most cases, the crude product obtained after removal of the solvent is of very high purity or sufficient purity and may be used immediately in subsequent reactions and conversions, in particular ester hydrolyses.

The pressure range of the reaction is uncritical and may be varied within wide limits. The pressure is customarily from 0.01 to 20 bar, and preference is given to carrying out the reaction under atmospheric pressure.

Preference is given to carrying out the reaction under inertization with protective gas such as nitrogen or argon. The reaction may be carried out continuously or batchwise, preferably batchwise.

All of the abovementioned symbols of the abovementioned formulae are each defined independently of one another.

DETAILED DESCRIPTION OF PREFERRED EMBODIMENTS

In the following examples, unless otherwise stated, all quantity and percentage data are based on weight, all pressures are 0.10 MPa (abs.) and all temperatures are 20° C.

EXAMPLE 1

Preparation of tert-Butyl 3-Hydroxy-3-phenylpropionate

At room temperature, a three-neck flask equipped with a reflux condenser, internal thermometer, dropping funnel and stirrer under nitrogen protective gas was initially charged with 8 g of zinc powder (122 mmol) in 47 ml of ethyl acetate. After 1.9 ml of trimethylchlorosilane (15 mmol) had been added, the mixture was heated to 60° C. for 15 min, then allowed to cool to 55° C. and 22 g of undiluted tert-butyl bromoacetate (113 mmol) were subsequently added dropwise within 5 min, and the temperature was maintained at 65° C. by external cooling. The mixture was then stirred at 50° C. for 10 min. After cooling to 0° C., 10 g of undiluted benzaldehyde (94 mmol) were added, and the temperature was maintained at 10° C. by external cooling. After stirring had been continued at 25° C. for 90 min and 35° C. for 15 min, 40 ml of ethyl acetate were added, the mixture was cooled to 15° C., acidified with 17 ml of 20% hydrochloric acid to a pH of 1–2 and the mixture was stirred for 10 min, during which excess zinc dissolved. The organic phase was then removed. The organic phase was then stirred with 15 ml of concentrated ammonia solution at 25° C. for 10 min. After the phase separation, drying was effected over sodium sulfate and the solvent was distilled off under reduced pressure. Tert-butyl 3-hydroxy-3-phenylpropionate was obtained in a yield of 20.3 g (97% of theory) and had a boiling point of 102° C. (1.5 mbar).

Similar preparation in the solvents methyl acetate, isopropyl acetate and n-butyl acetate produced tert-butyl 3-hydroxy-3-phenylpropionate in yields of 19.9 g, 20.5 g and 20.1 g (95, 98 and 96% of theory, respectively).

EXAMPLE 2

Preparation of Methyl 3-Hydroxy-3-phenylpropionate

At room temperature, a three-neck flask equipped with a reflux condenser, internal thermometer, dropping funnel and stirrer under nitrogen protective gas was initially charged with 7.6 g of zinc powder (115 mmol) in 45 ml of isopropyl acetate. After 1.83 ml of trimethylchlorosilane (14 mmol) had been added, the mixture was heated to 60° C. for 15 min, then allowed to cool to 55° C. and 16.3 g of undiluted methyl bromoacetate (107 mmol) were subsequently added dropwise within 5 min, and the temperature was maintained at 60° C. by external cooling. The mixture was then stirred at 50° C. for 15 min. After cooling to 30° C., 9.4 g of undiluted benzaldehyde (89 mmol) were added, and the temperature was maintained at 40° C. by external cooling. After stirring had been continued at 40° C. for 30 min, the mixture was cooled to 0° C., acidified with 20 ml of 20% hydrochloric acid to a pH of 1 and the mixture was stirred for 30 min, during which excess zinc dissolved. The organic phase was then removed. The organic phase was then stirred with 30 ml of concentrated ammonia solution at 0° C. for 10 min. After the phase separation, drying was effected over sodium sulfate and the solvent was distilled off under reduced pressure. Methyl 3-hydroxy-3-phenylpropionate was obtained in a yield of 14.3 g (89% of theory) and had a boiling point of 78° C. (0.08 mbar).

When ethyl bromoacetate was used, ethyl 3-hydroxy-3-phenylpropionate was prepared in a yield of 91% of theory.

EXAMPLE 3
Preparation of Methyl 3-Hydroxydecanoate

At room temperature, a three-neck flask equipped with a reflux condenser, internal thermometer, dropping funnel and stirrer under nitrogen protective gas was initially charged with 7.1 g of zinc powder (108 mmol) in 42 ml of ethyl acetate. After 1.7 ml of trimethylchlorosilane (13.4 mmol) had been added, the mixture was heated to 60° C. for 15 min, then allowed to cool to 55° C. and 15.3 g of undiluted methyl bromoacetate (100 mmol) were subsequently added dropwise within 7 min, and the temperature was maintained at 65° C. by external cooling. The mixture was then stirred at 50° C. for 15 min. After cooling to 0° C., 10.7 g of undiluted octanal (83 mmol) were added, and the temperature was maintained at 5° C. by external cooling. After stirring had been continued at 50C for 30 min, 25° C. for 2 h and 40° C. for 20 min, the mixture was cooled to 0° C., acidified with 30 ml of 10% hydrochloric acid to a pH of 1 and the mixture was stirred for 10 min. Excess zinc was then filtered off and the organic phase removed. The organic phase was then stirred with 10 ml of concentrated ammonia solution at 0° C. for 10 min. After the phase separation, drying was effected over sodium sulfate and the solvent was distilled off under reduced pressure. Methyl 3-hydroxydecanoate was obtained in a yield of 14.2 g (84% of theory) and had a boiling point of 59° C. (0.04 mbar).

Similar preparation in the solvent isopropyl acetate produced methyl 3-hydroxydecanoate in a yield of 15.6 g (87% of theory).

EXAMPLE 4
Preparation of Methyl 3-Hydroxy-3-(2-phenylethyl) hexanoate

At room temperature, a three-neck flask equipped with a reflux condenser, internal thermometer, dropping funnel and stirrer under nitrogen protective gas was initially charged with 7.9 g of zinc powder (121 mmol) in 45 ml of isopropyl acetate. After 1.83 ml of trimethylchlorosilane (12.6 mmol) had been added, the mixture was heated to 60° C. for 15 min, then allowed to cool to 55° C. and 17.7 g of methyl bromoacetate (115 mmol) were added within 5 min, and the temperature of the mixture was maintained at 60° C. by external cooling. The mixture was then stirred at 50° C. for 15 min. After cooling to 40° C., 15.7 g of undiluted 1-phenylhexan-3-one (89 mmol, prepared by base-catalyzed aldol condensation of benzaldehyde and pentan-2-one and subsequent hydrogenation of the 1-phenylhex-1-en-3-one obtained) were added, and the temperature was maintained at 50° C. by external cooling. The mixture was then stirred at 60° C. for 45 min and, after cooling to 15° C., acidified with 20 ml of 20% hydrochloric acid to a pH of 1 and stirred for 30 min. Excess zinc was then filtered off and the organic phase was removed. The organic phase was then stirred with 30 ml of concentrated ammonia solution at 0° C. for 10 min. After the phase separation, drying was effected over sodium sulfate and the solvent was distilled off under reduced pressure. Methyl 3-hydroxy-3-(2-phenylethyl)hexanoate was obtained in a yield of 21.1 g (95% of theory) and a purity of >95% (HPLC).

EXAMPLE 5
Preparation of Methyl 4-Hydroxy-4-phenylbutyrate

At room temperature, a three-neck flask equipped with a reflux condenser, internal thermometer, dropping funnel and stirrer under nitrogen protective gas was initially charged with 15.1 g of zinc powder (231 mmol) in 90 ml of isopropyl acetate. After 3.7 ml of trimethylchlorosilane (29 mmol) had been added, the mixture was heated to 60° C. for 20 min, then allowed to cool to 55° C. and 32.6 g of undiluted methyl bromoacetate (213 mmol) were subsequently added dropwise within 10 min, and the temperature was maintained at 60° C. by external cooling. The mixture was then stirred at 50° C. for 15 min. After cooling to 5° C., 21.3 g of undiluted styrene oxide (178 mmol) were added, and the temperature was maintained at 5° C. by external cooling. After stirring had been continued at 5° C. for 30 min, the mixture was heated to 25° C. within 20 min and stirred at this temperature for a further 30 min. After cooling to 0° C., the mixture was acidified using 33 ml of 20% hydrochloric acid to a pH of 1 and stirred for 30 min. Excess zinc was then filtered off and the organic phase removed. The organic phase was then stirred at 0° C. with 40 ml of 1 N hydrochloric acid and finally washed with 20 ml of concentrated ammonia solution. After the phase separation, drying was effected over sodium sulfate and the solvent was distilled off under reduced pressure (>90% of the solvent isopropyl acetate was recovered). After distillation, methyl 4-hydroxy-4-phenylbutyrate was obtained in a yield of 30.9 g (90% of theory) and had a boiling point of 128° C. (4 mbar).

Similar preparation in the solvents n-butyl acetate, ethyl acetate and methyl acetate delivered methyl 4-hydroxy-4-phenylbutyrate in yields of 29.5 g, 29.8 g and 28.1 g (86, 87 and 82% of theory, respectively).

EXAMPLE 6
Preparation of Methyl 3-(N-Phenylamino)-3-phenylpropionate

At room temperature, a three-neck flask equipped with a reflux condenser, internal thermometer, dropping funnel and stirrer under nitrogen protective gas was initially charged with 7.6 g of zinc powder (116 mmol) in 45 ml of isopropyl acetate. After 1.83 ml of trimethylchlorosilane (14.4 mmol) had been added, the mixture was heated to 60° C. for 15 min, then allowed to cool to 55° C. and 16.3 g of undiluted methyl bromoacetate (107 mmol) were subsequently added dropwise within 5 min, and the temperature was maintained at 60° C. by external cooling. The mixture was then stirred at 50° C. for 15 min. After cooling to 5° C., 16.1 g of benzalaniline (89 mmol) dissolved in 10 ml of isopropyl acetate were added and the mixture was heated to 25° C. After the mixture had been stirred at 25° C. for 1 h, it was heated to 40° C. for a further 10 min and then cooled to 5° C. Hydrolysis was then effected using 80 ml of concentrated ammonia solution. After 40 ml of isopropyl acetate had been added, the mixture was heated to 50° C. and precipitate formed went into solution. At this temperature, excess zinc was filtered off and the organic phase removed. The organic phase was then washed at 50° C. with 20 ml of water. After the phase separation, the solvent was distilled off under reduced pressure to give a crude product in a yield of 19.7 g (87% of theory) and a purity of >95% (HPLC). After recrystallization from ethyl acetate, methyl 3-(N-phenylamino)-3-phenylpropionate having a melting point of 110° C. was obtained.

COMPARATIVE EXAMPLE 7
Preparation of Methyl 4-Hydroxy-4-phenylbutyrate According to SU 472127

At room temperature, a three-neck flask equipped with a reflux condenser, internal thermometer, dropping funnel and stirrer under nitrogen protective gas was initially charged with 12.1 g of zinc powder (185 mmol) in 80 ml of ethyl acetate. After 2.5 ml of trimethylchlorosilane (20 mmol) had been added, the mixture was heated to 60° C. for 20 min, then allowed to cool to 55° C. and a mixture of 26.1 g of methyl bromoacetate (170 mmol) and 17 g of styrene oxide (142 mmol) was then added dropwise within 15 min while maintaining the temperature at 65° C. The mixture was then stirred at 60° C. for 60 min. After cooling to 0° C., the mixture was acidified using 24 ml of 20% hydrochloric acid to a pH of 3 and stirred for 10 min. Excess zinc was then filtered off and the organic phase removed. The organic phase was then stirred at 0° C. with 30 ml of 1 N hydrochloric acid and finally washed with 15 ml of concentrated ammonia solution. After the phase separation, drying was effected over sodium sulfate and the solvent distilled off under reduced pressure. In the mixture obtained, methyl 4-hydroxy-4-phenylbutyrate could not be detected analytically.

Accordingly, while a few embodiments of the present invention have been shown and described, it is to be understood that many changes and modifications may be made thereunto without departing from the spirit and scope of the invention as defined in the appended claims.

What is claimed is:

1. A process for preparing organozinc halides in a solvent, comprising reacting a reactive halogen compound with zinc in at least one carboxylic ester, to produce a solution.

2. The process for preparing organozinc halides of the general formula (4)

$$HalZn—R^3R^4C—(X)_l—Y \quad (4)$$

as claimed in claim 1, wherein reactive halogen compounds of the general formula (2)

$$Hal-R^3R^4C—(X)_l—Y \quad (2)$$

are reacted with zinc, where $R^1$ and $R^2$ are each hydrogen or an optionally halogen- or cyano-substituted $C_1$–$C_{30}$-hydrocarbon radical in which one or more nonadjacent methylene units may be replaced by —O—, CO—, —COO—, —OCO—, or —OCOO—, —S— or —NR$^x$— groups and in which one or more methine units may be replaced by —N═ or —P═ groups, $R^3$, $R^4$, $R^5$, $R^6$ and $R^7$ are each hydrogen, halogen or an optionally halogen-substituted or cyano-substituted $C_1$–$C_{30}$-hydrocarbon radical in which one or more nonadjacent methylene units may be replaced by —O—, —CO—, —COO—, —OCO—, or —OCOO—, —S— or —NR$^x$— groups and in which one or more methine units may be replaced by —N═ or —P═ groups, X is selected from

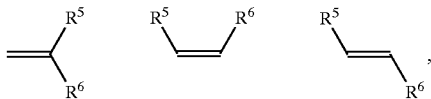

l is an integer having the value 0 or 1,

Y is CN, (C═O)—Z, (SO$_2$)—Z, (P═O)(—Z)$_2$, $R^5$C═CR$^6$R$^7$, C≡C—R$^5$ or an aromatic radical in which one or more methine units in the ring may be replaced by —N═ or —P═ groups and which may carry the heteroatoms —O—, —S— or —NH— in the ring, where the aromatic ring is optionally halogen- or cyano-substituted or is substituted by $C_1$–$C_{30}$-hydrocarbon radicals in which one or more nonadjacent methylene units may be replaced by —O—, —CO—, —COO—, —OCO—, or —OCOO—, —S— or —NR$^x$— groups, Z is an optionally halogen-substituted $C_1$–$C_{30}$-hydrocarbon radical in which one or more nonadjacent methylene units may be replaced by —O—, —CO—, —COO—, —OCO—, —OCOO—, —S— or —NR$^x$— groups and in which one or more methine units may be replaced by —N═ or —P═ groups, OH, OR$^1$, OSi(R$^3$)$_3$, NHR$^1$ or NR$^1$R$^2$, Hal is chlorine, bromine or iodine, R$^x$ is hydrogen or an optionally halogen-substituted $C_1$–$C_{30}$-hydrocarbon radical in which one or more nonadjacent methylene units may be replaced by —O—, —CO—, —COO—, —OCO—, or —OCOO—, —S—, —NH— or —N—$C_1$–$C_{20}$-alkyl groups and in which one or more methine units may be replaced by —N═ or —P═ groups, and pairs of radicals selected from $R^1$ and $R^2$, $R^3$ and $R^4$, $R^4$ and $R^5$, $R^5$ and $R^6$, $R^6$ and $R^7$, $R^1$ and $R^3$, $R^1$ and Y, $R^1$ and Z, $R^3$ and Y, $R^3$ and Z, $R^5$ and Y, $R^5$ and Z, where Z may be a direct bond, may in each case be linked to each other.

3. The process as claimed in claim 1, comprising using carboxylic esters of the general formula (3)

$$R^8—((O(CH_2)_m)_n—COO—((CH_2)_o—COO)_p—((CH_2)_qO)_r—R^9 \quad (3)$$

where $R^8$ and $R^9$ are each a $C_1$–$C_{30}$-hydrocarbon radical in which one or more nonadjacent methylene units may be replaced by —O— groups, and m, n, o, p, q and r are each integers having values of from 0 to 6.

4. The process as claimed in claim 1, comprising using bromine compounds as the reactive halogen compounds.

5. The process as claimed in claim 1, comprising using α-bromocarboxylic esters as the reactive halogen compounds.

6. The process as claimed in claim 1, in which carboxylic ester is selected from the group consisting of an alcohol selected from the group consisting of methyl alcohol, ethyl alcohol, n-propyl alcohol, i-propyl alcohol, n-butyl alcohol, i-butyl alcohol, t-butyl alcohol, n-hexyl alcohol, n-pentyl alcohol, i-pentyl alcohol with a carboxylic acid selected from the group consisting of acetic acid, propionic acid, butyric acid and ($C_6$–$C_{14}$)-alkyl acetate mixtures.

7. The process as claimed in claim 1, comprising activating the zinc used by using trimethylchlorosilane.

8. The solution prepared by the process according to claim 1.

9. A method for preparing a compound selected from the group consisting of a keto compound, a hydroxyl compound, and an amino compound of organozinc halides obtained in a first step for preparing an organozinc halide in a solvent by reacting a reactive halogen compound with zinc in at least one carboxylic ester; and in a second step, reacting the organozinc halide obtained in the first step with an electrophilic reaction partner to produce a reaction product; and in a third step, hydrolyzing the reaction product of the second step.

10. A method for preparing a compound selected from the group consisting of a keto compound, a hydroxyl compound, and an amino compound of organozinc halides obtained in a first step for preparing an organozinc halide in a solvent by reacting a reactive halogen compound with zinc in at least one carboxylic ester; and in a second step, reacting the organozinc halide obtained in the first step with an electrophilic reaction partner to produce a reaction product; and in a third step, hydrolyzing the reaction product of the second step;

wherein the keto compound, the hydroxyl compound and the amino compound each have the general formula (1)

$$R^1(R^2)_kC(W^x)\text{—}R^3R^4C\text{—}(X)_1\text{—}Y \tag{1}$$

wherein the electrophilic reaction partner used in the second step is an aldehyde, a ketone or an imine of the general formula (5a)

$$R^1R^2C\text{=}W \tag{5a}$$

or an epoxide of the general formula (5b)

(5b)

or a nitrile of the general formula (5c)

$$R^1C\text{≡}N \tag{5c}$$

or a carboxylic halide of the general formula (5d)

$$R^1(C\text{=}O)\text{-Hal} \tag{5d}$$

where
$W^x$ is OH, NHR$^1$ or =O and
W is O or NR$^1$,
k, when $W^x$ is OH and NHR$^1$, should have the value 1 and, when $W^x$ is =O, should have the value 0, and
the remaining radicals are defined in claim 2, and also pairs of 2 radicals selected from R$^1$ and R$^2$, R$^3$ and R$^4$, R$^4$ and R$^5$, R$^5$ and R$^6$, R$^6$ and R$^7$, R$^1$ and R$^3$, R$^1$ and Y, R$^1$ and Z, R$^3$ and Y, R$^3$ and Z, R$^5$ and Y, R$^5$ and Z, W$^1$ and Y and also W$^1$ and Z, where $W^x$ is O— or NR$^1$— and Z may be a direct bond, may each be linked to each other.

* * * * *